(12) United States Patent
Chen et al.

(10) Patent No.: US 12,391,969 B2
(45) Date of Patent: Aug. 19, 2025

(54) ADDITIVE USED IN METHIONINE PREPARATION PROCESS, AND METHIONINE PREPARATION METHOD

(71) Applicants: ZHEJIANG NHU CO., LTD., Zhejiang (CN); SHANDONG NHU AMINO ACID CO., LTD., Shandong (CN)

(72) Inventors: Zhirong Chen, Zhejiang (CN); Hong Yin, Zhejiang (CN); Zhixuan Wang, Shandong (CN); Cong Chen, Shandong (CN); Shuangshuang Zhang, Shandong (CN); Yu Wang, Zhejiang (CN)

(73) Assignees: ZHEJIANG NHU CO., LTD., Zhejiang (CN); SHANDONG NHU AMINO ACID CO., LTD., Shandong (CN)

( * ) Notice: Subject to any disclaimer, the term of this patent is extended or adjusted under 35 U.S.C. 154(b) by 626 days.

(21) Appl. No.: 17/782,904

(22) PCT Filed: Oct. 20, 2020

(86) PCT No.: PCT/CN2020/122134
§ 371 (c)(1),
(2) Date: Jun. 6, 2022

(87) PCT Pub. No.: WO2021/135523
PCT Pub. Date: Jul. 8, 2021

(65) Prior Publication Data
US 2023/0022196 A1 Jan. 26, 2023

(30) Foreign Application Priority Data
Dec. 31, 2019 (CN) .......................... 201911412213.4

(51) Int. Cl.
*C12P 13/12* (2006.01)
*B01D 9/00* (2006.01)
*C07C 319/26* (2006.01)

(52) U.S. Cl.
CPC ............ *C12P 13/12* (2013.01); *B01D 9/0013* (2013.01); *C07C 319/26* (2013.01); *C07B 2200/13* (2013.01)

(58) Field of Classification Search
CPC ...... C12P 13/12; B01D 9/0013; C07C 319/26
See application file for complete search history.

(56) References Cited

U.S. PATENT DOCUMENTS

2021/0251856 A1* 8/2021 Sirichandra ............ A61K 8/442

FOREIGN PATENT DOCUMENTS

| CN | 1473145 | A | 2/2004 |
|---|---|---|---|
| CN | 1599712 | A | 3/2005 |
| CN | 104203912 | A | 12/2014 |
| CN | 105418933 | A | 3/2016 |
| CN | 105646304 | A | 6/2016 |
| CN | 105764886 | A | 7/2016 |
| EP | 1256571 | A1 | 11/2002 |
| EP | 3187489 | A1 | 7/2017 |
| JP | S4619610 | B1 | 6/1971 |
| JP | H04169570 | A | 6/1992 |
| JP | H04244056 | A | 9/1992 |
| JP | H10306071 | A | 11/1998 |

(Continued)

OTHER PUBLICATIONS

International Search Report issued in corresponding International PCT Application No. PCT/CN2020/122134; Mailing date: Jan. 7, 2021.

(Continued)

*Primary Examiner* — Yong L Chu
(74) *Attorney, Agent, or Firm* — Chrisman Gallo Tochtrop LLC

(57) ABSTRACT

The present disclosure relates to an additive used in a methionine preparation process, and a methionine preparation method. The additive provided by the present disclosure is a mixture containing components A, B, and C; component A has a structure represented by the following general formula (1); component B has a structure represented by the following general formula (2); component C is silicone oil; $RCON(CH_3)CH_2CH_2SO_3Na$ (1). The methionine preparation method provided in the present invention comprises subjecting methionine to crystallization and/or recrystallization in the presence of the additive provided by the present disclosure. The additive provided by the present disclosure results in uniform emulsification, has good stability, can be used stably for a long time, and is suitable for a continuous crystallization process. The prepared methionine crystal has a good crystal form, a large bulk density, and good flowability. In addition, according to the methionine preparation method of the present disclosure, a crystallization system can operate continuously and stably for a long time without obvious foaming, and the crystallization process of the methionine product can proceed smoothly.

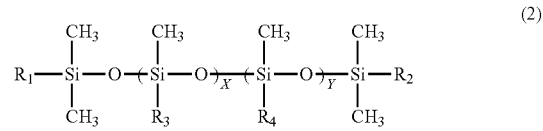

20 Claims, 1 Drawing Sheet

(56) References Cited

FOREIGN PATENT DOCUMENTS

JP        H11158140 A    6/1999
JP        2004292324 A   10/2004

OTHER PUBLICATIONS

Li et al., "Synthesis and Properties of Modified Polsiloxanes Defoaming Agents", Journal of Changchun University of Science and Technology, vol. 129, No. 2, pp. 1-3, Jun. 2006.

* cited by examiner

ADDITIVE USED IN METHIONINE PREPARATION PROCESS, AND METHIONINE PREPARATION METHOD

TECHNICAL FIELD

The present disclosure relates to additives used in the crystallization process of methionine and methods of use thereof, in particular to additives comprising a compound having a defoaming action and a compound capable of regulating crystal growth using in the crystallization process, and methods for preparing methionine.

BACKGROUND

Methionine is one of the amino acids necessary for animal growth. It is involved in protein synthesis and is the only sulfur-containing amino acid. It is used as a nutrition fortifier for feeds to improve the amino acid balance.

Existing methionine is mainly synthesized by chemical methods. Depending upon the difference in raw material routes, the main method for synthesis includes a malonate method, an acraldehyde method, or an amino lactone method etc. In contrast, the synthetic route of condensing hydrocyanic acid and a salt thereof with methylthiopropanal to prepare 5-(2-methylthioethyl)-hydantoin, followed by hydrolysis with potassium carbonate and acidification with carbon dioxide for reaction crystallization is the most competitive route.

During the above synthesis process, serious foaming occurs as a result of carrying out acidification with gaseous carbon dioxide for reaction crystallization, which renders the crystallization process unable to proceed continuously and smoothly. Moreover, the methionine crystals obtained by reaction crystallization or cooling recrystallization all have scale-like crystal forms, and they have a low bulk density and poor flowability, and are liable to powder floating, which causes inconvenience for subsequent use.

In order to control the foaming in the reaction crystallization process and to obtain better crystal morphology, EP1256571A1 discloses a process for liberating methionine from the aqueous solution of alkali metal methioninate with carbon dioxide. The process comprises adding a defoaming agent to the aqueous solution containing alkali metal methioninate before liberation of the methionine. All compounds that have a foam-inhibiting function are suitable as defoaming agents. The defoaming agent is introduced into the solution preferably in the form of dispersion, so as to promote the effect of the defoaming agent on the reaction crystallization process of methionine, and particularly to prevent the formation of crystal products with thin leaves or flakes. Spherical crystals are obtained and are largely free from dust after drying.

The Sumitomo Chemical Company has proposed to add additives when carrying out the reaction crystallization with carbon dioxide in JPH04244056A, JPH11-158140A, and JPH04-169570A, respectively. The additives used in these patent literatures are casein or semi-synthetic cellulose-based water-soluble polymers (including methyl cellulose, ethyl cellulose, hydroxyethyl methyl cellulose, hydroxyethyl cellulose, and hydroxypropyl methyl cellulose); aggregating agents (sorbitan monolaurate, polyvinyl alcohol, hydroxypropyl methyl cellulose, etc.); and polyvinyl alcohol, respectively. The resulting methionine crystals are granules or thick flakes with a bulk density of 0.55 to 0.60 g/cc.

In JPH10-306071A and JP2004-292324A, the Nippon Soda Company discloses adding polyvinyl alcohol or gluteline to precipitate the DL-methionine crystal from a solution containing DL-methionine, thereby producing a granular DL-methionine crystal product with a specific volume of 1.3 to 1.6 mL/g.

The granular methionine crystals obtained by the above-mentioned method are actually agglomerates of scale-like crystals. They have a low bulk density and are prone to breakage and powder floating after suffering from extrusion during drying and use, so they are inconvenient for subsequent use.

In JPS46-019610, the Sumitomo Corporation describes a method for recrystallizing methionine, in which additives and defoaming agents are also added during recrystallization. The additives are nonionic surfactants (e.g., oxyethylene fatty acid esters, alkylphenol ethoxylates, polyoxyethylene-polyoxypropylene, or sorbitan fatty acid ester) or anionic surfactants (e.g., nonane sulfonates, alkyl naphthalene sulfonates, alkylbenzene sulfonates, or dialkyl sulfonate succinates). However, the bulk density of the product is not high.

To obtain methionine crystals with a high bulk density, the Degussa Company has proposed in CN1599712A (Authorized Announcement No.: CN1332926C) to add additive (1) and additive (2) before converting 5-(2-methylthioethyl)-hydantoin into methionine and charging carbon dioxide. The additive (1) has the following structural formula:

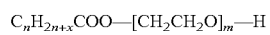

n: 9 to 19; m: in the range of from 1 to 10; x: 1, −1, −3, −5, where 2n+x≥1.

The additive (2) is selected from modified celluloses, specifically methyl cellulose, methyl hydroxy celluloses, methyl hydroxypropyl celluloses, hydroxypropyl celluloses, hydroxyethyl celluloses, sodium carboxymethyl celluloses, sodium carboxymethyl hydroxyethyl celluloses, or sodium carboxymethyl hydroxypropyl celluloses, preferably hydroxyethyl celluloses. The recrystallized methionine product obtained by this method has a better crystal form, and has a maximum bulk density of 620 g/L.

In CN104203912A, the Evonik Industries AG has proposed to obtain a crude methionine crystal by feeding the carbon dioxide to a hydrolysate of crude 5-(2-methylthioethyl)-hydantoin. For the sake of purification, the crude methionine is recrystallized in the presence of a crystallization additive that is a nonionic or anionic surfactant, or a mixture of different nonionic or anionic surfactants, and of a defoaming agent. The crystallization additive is either of additive (1) and additive (2). The crystallization additive (1) is one of the compounds represented by the following three structural formulae, or a mixture thereof:

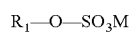

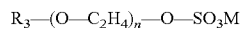

where n is an integer from 1 to 12, preferably n=2; M is sodium or potassium; and $R_1$ to $R_3$ are a linear, branched or cyclic, saturated or unsaturated $C_8$ to $C_{20}$ alkyl group or an aryl group, preferably $R_1$, $R_2$ and $R_3$ are linear, saturated $C_8$ to $C_{18}$ alkyl group.

The additive (2) is a sorbitan fatty acid ester or a mixture of different sorbitan fatty acid esters, preferably polyethoxylated sorbitan fatty acid esters, and in particular a polyethoxylated sorbitan tristearate.

The defoaming agent comprises silicone oil, and further comprises constituents which are effective as emulsifiers (preferably mixtures of polyethoxylated fatty acids and polyethoxylated fatty alcohols). Further, the defoaming agent likewise comprises silica.

The methionine obtained by this method has a bulk density of 537 to 651 g/L.

In CN105764886A, the Evonik Degussa GmbH has proposed to crystalize D,L-methionine in the presence of a crystallization additive and a defoaming agent. The crystallized additive used comprises a nonionic or anionic surfactant or a mixture of various nonionic or anionic surfactants. The anionic surfactant is one of the compounds depicted in the following three structural formulae, or mixtures thereof:

$C_nH_{2n+1}$—O—$SO_3$Na, where n=12-18
(Sulfopon®1218G,Oleochemicals)

$C_nH_{2n+1}$—O—$C_2H_4$—$SO_3$Na, where n=8-18(Hostapon® SCI85,Clariant)

$C_nH_2n+1$—(O$C_2H_4$)$_2$—O—$SO_3$Na, where n=12(Disponil® FES27,Cognis).

The nonionic surfactant used is a sorbitan fatty acid ester or a mixture of various sorbitan fatty acid esters, particularly preferably a polyethoxylated sorbitan tristearate.

Moreover, the defoaming agent comprises silicone oil, further comprises constituents which are effective as emulsifiers (preferably mixtures of polyethoxylated fatty acids and polyethoxylated fatty alcohols), and may further comprise silica.

The recrystallized methionine product obtained by this method has a maximum bulk density of 651 g/L.

All of the additives used in the above-mentioned methods contain ester bonds, which are prone to hydrolysis at a higher temperature for methionine formulation, thereby losing their regulating or defoaming effect. As a result, this tends to render the crystallization process unstable on the condition of recycling crystallization mother liquor, thereby affecting the stable operation of the continuous crystallization process. Moreover, there still remains room for improving the bulk density of the methionine crystal products.

SUMMARY

In view of the problems existing in the literatures, the present disclosure provides an additive for use in a methionine preparation process, and a method for preparing methionine. By using such an additive, it is possible to prepare methionine crystal products having a high bulk density and good flowability.

The present disclosure provides an additive for use in a methionine preparation process, wherein the additive is a mixture comprising components A, B and C, the component A has a structure represented by the following general formula (1):

$$RCON(CH_3)CH_2CH_2SO_3Na \quad (1)$$

in formula (1), R is a saturated or unsaturated $C_7$-$C_{36}$ hydrocarbyl group, preferably a $C_7$-$C_{36}$ alkyl or alkenyl group;

the component B has a structure represented by the following general formula (2):

$$\begin{array}{c} CH_3 \quad CH_3 \quad CH_3 \quad CH_3 \\ | \quad\quad | \quad\quad | \quad\quad | \\ R_1-Si-O-(Si-O)_X-(Si-O)_Y-Si-R_2 \\ | \quad\quad | \quad\quad | \quad\quad | \\ CH_3 \quad R_3 \quad R_4 \quad CH_3 \end{array} \quad (2)$$

in formula (2), X and Y are each an integer of 1 to 30, $R_1$ to $R_4$ are the same as or different from one another, and each independently represent H, an $C_1$-$C_3$ alkyl group, a saturated or unsaturated aliphatic hydroxyl group, or a saturated or unsaturated polyether group, provided that at least one of $R_1$ to $R_4$ represents the saturated or unsaturated polyether group, the polyether group being more preferably a group represented by the following general formula (3):

$$—C_3H_6O(C_2H_4O)_a(C_3H_6O)_bR_0 \quad (3)$$

in formula (3), a represents an integer of 0 to 50, b represents an integer of 0 to 50, and $R_0$ represents H, an alkyl group, an acyloxyl group, or an alkoxyl group; and the component C is silicone oil.

The additive for use in the methionine preparation process provided in the present disclosure, wherein the component A is one or more of sodium methyl octanoyl taurate, sodium methyl decanoyl taurate, sodium methyl lauroyl taurate, sodium methyl myristoyl taurate, sodium methyl palmitoyl taurate, sodium methyl stearoyl taurate, sodium methyl oleyl taurate, sodium methyl linoleoyl taurate, sodium methyl linolenoyl taurate, sodium methyl erucoyl taurate, sodium methyl cocoyl taurate, sodium methyl palmitoyl taurate, sodium methyl soybean oil fatty acyl taurate, sodium methyl peanut oil fatty acyl taurate, sodium methyl sesame oil fatty acyl taurate, sodium methyl mustard oil fatty acyl taurate, sodium methyl hardened tallow fatty acyl taurate, and sodium methyl hardened vegetable oil fatty acyl taurate; and preferably one or more of sodium methyl lauroyl taurate, sodium methyl myristoyl taurate, sodium methyl palmitoyl taurate, sodium methyl stearoyl taurate, sodium methyl cocoyl taurate, and sodium methyl palmitoyl taurate.

The additive for use in the methionine preparation process provided in the present disclosure, wherein the component B has a molecular weight of from 1,000 to 10,000, preferably from 3,000 to 6,000.

The additive for use in the methionine preparation process provided in the present disclosure, wherein the component B has an HLB value of from 7 to 15, preferably from 9 to 12.

The additive for use in the methionine preparation process provided in the present disclosure, wherein the component B is polyether-grafted silicone oil, preferably allyl polyoxyalkyl ethers-grafted silicone oil.

The additive for use in the methionine preparation process provided in the present disclosure, wherein the component C comprises one or more of dimethyl silicone oil, hydroxyl silicone oil, and hydrogen-containing silicone oil, and preferably the component C has a dynamic viscosity at 25° C. of 90 mm$^2$/s to 1,500 mm$^2$/s.

The additive for use in the methionine preparation process provided in the present disclosure, wherein the additive is an aqueous mixture comprising the components A, B and C, and based on a total mass of the additive, the content of the component A is from 1 to 8 wt %, and the content of the component B is from 0.5 to 8 wt %, and the content of the component C is from 0.5 to 4 wt %; and preferably, the content of the component A is from 2 to 6 wt %, the content of the component B is from 2 to 6 wt %, and the content of the component C is from 1 to 3 wt %.

The present disclosure further provides a method for preparing methionine, comprising:

subjecting methionine to crystallization and/or recrystallization in the presence of the additive provided in the present disclosure.

The preparation method for methionine provided in the present disclosure, comprising the steps of:
(1) subjecting an aqueous methionate solution obtained from hydrolysis of 5-(2-methylthioethyl)-hydantoin to reaction crystallization in the presence of an additive and carbon dioxide, to obtain a crude methionine crystal product; and
(2) forming a methionine suspension from the crude methionine crystal product, water and/or crystallization mother liquor, adding an additive, and recrystallizing a resulting additive-containing methionine solution, to obtain a methionine crystal product.

The preparation method for methionine provided in the present disclosure, wherein an amount of the additive in the step (1) is from 50 ppm to 500 ppm, preferably from 70 ppm to 300 ppm, based on a total mass of the aqueous methionate solution.

The preparation method for methionine provided in the present disclosure, wherein the methionine suspension in the step (2) has a concentration of from 8 to 15 wt %, preferably from to 13 wt %.

The preparation method for methionine provided in the present disclosure, wherein an amount of the additive in the step (2) is from 100 ppm to 1,000 ppm, preferably from 200 ppm to 500 ppm, based on a total mass of the methionine suspension.

The preparation method for methionine provided in the present disclosure, wherein in the step (2), the crystallization is carried out by means of refrigerative cooling or evaporative cooling, preferably by means of the evaporative cooling; and
when the crystallization is carried out by the evaporative cooling, vapor generated by evaporation is pressurized by a vapor compressor to raise temperature, and is then used in a heating and dissolving process of the methionine suspension.

The preparation method for methionine provided in the present disclosure, wherein a crystallizer used in the step (2) includes a stirring crystallization kettle, a forced-circulating crystallizer (FC crystallizer), an OSLO crystallizer, and a draft-tube-baffled crystallizer (DTB crystallizer); and preferably an FC crystallizer, an OSLO crystallizer, and a DTB crystallizer.

The additive used in the preparation process of methionine and the preparation method for methionine provided in the present disclosure achieve the following beneficial effects:

The additive provided in the present disclosure is handy, and at the time of forming an emulsification system during reaction crystallization and recrystallization for preparation of methionine, the emulsification is uniform, and the system is stable and is not easily layered. Moreover, the additive provided in the present disclosure has good stability, is not easy to decompose during the continuous recycling process, and can be used stably for a long time, which is applicable for a continuous crystallization process. The methionine crystals prepared using the additive of the present disclosure have a good crystal form, a high bulk density of 786 g/L or more and even up to 802 g/L, and good flowability, which is convenient for subsequent use. In addition, the preparation method for methionine according to the present disclosure allows the crystallization system to operate continuously and stably for a long time without obvious foaming, and allows the crystallization process of methionine products to proceed smoothly.

DETAILED DESCRIPTION

Figure 1:
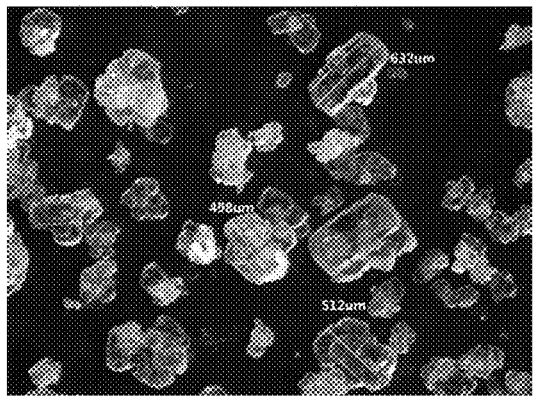
FIGS. 1 to 5 show microscope photographs of methionine crystals corresponding to Examples 1 to 5, respectively.

The additive used in the preparation process of methionine provided in the present disclosure is a mixture comprising components A, B, and C. Moreover, in the preferred embodiments of the present disclosure, the additive is used in the form of a water-containing mixture.

The component A is a crystal growth regulator, and has a structure represented by the following general formula (1):

$$RCON(CH_3)CH_2CH_2SO_3Na \qquad (1)$$

in formula (1), R is a saturated or unsaturated $C_7$-$C_{36}$ hydrocarbyl group, preferably a $C_7$-$C_{36}$ alkyl or alkenyl group.

Specific examples of the component A include one or more of sodium methyl octanoyl taurate, sodium methyl decanoyl taurate, sodium methyl lauroyl taurate, sodium methyl myristoyl taurate, sodium methyl palmitoyl taurate, sodium methyl stearoyl taurate, sodium methyl oleyl taurate, sodium methyl linoleoyl taurate, sodium methyl linolenoyl taurate, sodium methyl erucoyl taurate, sodium methyl cocoyl taurate, sodium methyl palmitoyl taurate, sodium methyl soybean oil fatty acyl taurate, sodium methyl peanut oil fatty acyl taurate, sodium methyl sesame oil fatty acyl taurate, sodium methyl mustard oil fatty acyl taurate, sodium methyl hardened tallow fatty acyl taurate, and sodium methyl hardened vegetable oil fatty acyl taurate.

Preferably, the component A is one or more of sodium methyl lauroyl taurate, sodium methyl myristoyl taurate, sodium methyl palmitoyl taurate, sodium methyl stearoyl taurate, sodium methyl cocoyl taurate, and sodium methyl palmitoyl taurate.

Generally, specific compounds of the above-mentioned component A are commercially available.

In the additive provided in the present application, the component A is featured with extremely low irritation, non-toxicity, and easy-biodegradation, and has good biodegradation. This substance can be decomposed into fatty acids and amino acids by enzymes in animal bodies, which can be utilized in animal bodies. Further, compared with the ester additives used in the prior art, the additive of the present disclosure has better hydrolytic stability, and thus it can be circulated in the system for a long time, and can stably function as a crystal growth regulator.

The above-mentioned component B is an emulsified foam inhibitor, which mainly has a foam inhibitory effect and an emulsification effect, and has a structure represented by the following general formula (2):

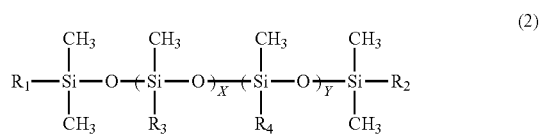

in formula (2), X and Y are each an integer of 1 to 30, $R_1$ to $R_4$ are the same as or different from one another, and each independently represent H, an $C_1$-$C_3$ alkyl group, a saturated or unsaturated aliphatic hydroxyl group, or a saturated or unsaturated polyether group; when at least one of $R_1$ to $R_4$ represents the saturated or unsaturated polyether group, the polyether group being more preferably a group represented by the following general formula (3):

—$C_3H_6O(C_2H_4O)_a(C_3H_6O)_bR_0$     (3)

where a represents an integer of 0 to 50, b represents an integer of 0 to 50, and $R_0$ represents H, an alkyl group, an acyloxyl group, or an alkoxyl group; and the component B has a molecular weight of from 1,000 to 10,000, preferably from 3,000 to 6,000, and has an HLB value of from 7 to 15, preferably from 9 to 12.

The component B is preferably polyether-modified silicone oil. In a more preferred embodiment, the component B is allyl polyoxyalkyl ethers-grafted silicone oil. The component B is even more preferably polyoxyethylene polyoxypropylene ether-grafted silicone oil.

The component B can be self-emulsified in water or miscible with water in an arbitrary ratio. Thus, during crystallization and filtration of methionine, almost all of the component B enters the water phase without attaching to the surface of methionine products. As a result, its defoaming action can be maintained stably for a long time. The component B is considered to have the defoaming, foam inhibitory and emulsifying functions when used under the conditions of the present disclosure, and it plays a main role in foam inhibition and emulsification.

In the preparation process of methionine, a large amount of foams is generated due to a need to charge carbon dioxide into the crude methionine crystal product, and meanwhile, the addition of the component A during the recrystallization of methionine also results in lots of foams. These foams have impacts on the stable operation of the system, and on the morphology and bulk density of the product, so there is a need to inhibit the foams using the component B. In the presence of the component B can the component A and the component C be in an emulsified state and be dispersed in the system.

The component C is silicone oil with an intensified defoaming action. It eliminates foams generated in the crystallization process, stabilizes the crystallization environment, improves the smoothness of crystals, and imparts good flowability to the products.

The component C comprises dimethyl silicone oil, hydroxyl silicone oil, or hydrogen-containing silicone oil. Preferably, the component C has a dynamic viscosity at 25° C. of 90 mm$^2$/s to 1,500 mm$^2$/s.

By using the additive of the present disclosure during hydrolysis of 5-(2-methylthioethyl)-hydantoin and acidification with carbon dioxide for reaction crystallization and recrystallization, under the synergistic effect of components A, B and C, it is possible to produce powdery methionine crystal products with a higher bulk density and better flowability, and enable the crystallization system to operate continuously and stably for a long time without obvious foaming, and the crystallization process of methionine products to proceed smoothly and steadily. Also, the additive according to the present disclosure can exhibit its effects on defoaming, foam inhibition, and crystal growth promotion when added in a small amount.

The total content of the components A, B and C is 2% to 20%, preferably 5% to 15% of the total weight of the additive in the form of an aqueous mixture, and the remaining is water.

Preferably, for the sake of allocation and uniform distribution of the additive, the additive of the present disclosure is used in the form of an aqueous mixture. Moreover, the above-mentioned components A, B and C are each present in the additive in a specific proportion. Specifically, based on the total mass of the additive, the content of the component A is from 1 to 8 wt %, the content of the component B is from 0.5 to 8 wt %, and the content of the component C is from 0.5 to 4 wt %; and preferably, the content of the component A is from 2 to 6 wt %, the content of the component B is from 2 to 6 wt %, and the content of the component C is from 1 to 3 wt %. If the content of the components A, B and C is not within the above-mentioned ranges, it is impossible to form a stable emulsifier, and the components cannot be uniformly dispersed in the system, and thus cannot achieve the desired effects. If the content of any one of the three components is not within the above-mentioned range, the balance of synergism of the additive will be upset, thereby weakening the desired effects.

The method for preparing methionine provided in the present disclosure comprises subjecting methionine to crystallization and/or recrystallization in the presence of the additive according to the present disclosure.

Preferably, the preparation method of methionine according to the present disclosure comprises the steps of:
(1) subjecting an aqueous methionate solution obtained from hydrolysis of 5-(2-methylthioethyl)-hydantoin to reaction crystallization in the presence of the additive and carbon dioxide, to obtain a crude methionine crystal product; and
(2) forming a methionine suspension from the crude methionine crystal product, water and/or crystallization mother liquor, and recrystallizing an additive-containing methionine solution obtained by dissolving the methionine suspension together with the additive, to obtain a methionine crystal product.

To be specific, the preparation method of methionine according to the present disclosure comprises:
(1) adding the additive according to the present disclosure to an aqueous methionate solution obtained from hydrolysis of 5-(2-methylthioethyl)-hydantoin, charging carbon dioxide while stirring, precipitating a methionine crystal by means of reaction crystallization, and filtering the methionine crystal to obtain a crude methionine crystal product; and
(2) mixing the aforesaid crude methionine crystal product with water and/or crystallization mother liquor to obtain a methionine suspension, adding the additive, and completely dissolving the crude methionine crystal product by stirring at a temperature of 90° C. to 110° C. to obtain an additive-containing methionine solution; and recrystallizing the additive-containing methionine solution at a temperature of 25° C. to 65° C., and subjecting the resulting crystallization slurry to filtration, washing and drying to obtain a methionine crystal product.

The crystallization mother liquor may be crystallization mother liquor resulting from filtration after the recrystallization in step (2) in the preparation method for methionine according to the present disclosure, or mixed liquor of the crystallization mother liquor resulting from filtration after the crystallization in step (1) and the crystallization mother liquor resulting from filtration after the recrystallization in step (2) in the preparation method for methionine according to the present disclosure.

In the preparation method for methionine provided in the present disclosure, the 5-(2-methylthioethyl)-hydantoin used in step (1) is commercially available.

In step (1), the method for precipitating a methionine crystal product by producing an aqueous methionate solution from hydrolysis of 5-(2-methylthioethyl)-hydantoin, and then charging carbon dioxide is commonly employed in the art, and the operation conditions may be those commonly used in the art. For example, the method may be a method for obtaining potassium methionate by hydrolyzing 5-(2-methylthioethyl)-hydantoin at 120 to 250° C. and 5 to 30 bar in the presence of potassium hydroxide, potassium carbonate and/or potassium bicarbonate or a mixture thereof, and then liberating a methionine crystal from the aqueous potassium methionate solution with carbon dioxide.

Further, the amount of the additive in the step (1) is from 50 ppm to 500 ppm, preferably from 70 ppm to 300 ppm, based on a total mass of the aqueous methionate solution. In the step (1), if the addition amount of the additive exceeds the upper limit of the above-mentioned range, the defoaming agent will be accumulated, leading to a decrease in bulk density and an increase in cost; if it is less than the lower limit of the above-mentioned range, the additive does not work as intended.

According to the preparation method for methionine provided in the present disclosure, in step (2), the process of obtaining the additive-containing methionine solution by dissolving the crude methionine together with the additive and water and/or crystallization mother liquor is usually carried out in a stirring vessel; thereafter, the additive-containing methionine solution is fed into the crystallizer preferably in a continuous state, and is crystallized therein continuously.

In step (2), the concentration of the additive-containing methionine solution is from 8 to 15 wt %, preferably from 10 to 13 wt %. If the concentration of the additive-containing methionine solution is too low, plenty of water needs to be removed by evaporation in the subsequent stages, resulting in higher costs; if the concentration is too high, the crude methionine crystal cannot be fully dissolved, and as a result, the crystal growth during recrystallization cannot achieve the desired effect.

In step (2), the addition amount of the additive is from 100 ppm to 1,000 ppm, preferably from 200 ppm to 500 ppm, based on the total mass of the methionine suspension. In the step (2), if the addition amount of the additive exceeds the upper limit of the above-mentioned range, the defoaming agent will be accumulated, leading to a decrease in bulk density and an increase in cost; if it is less than the lower limit of the above-mentioned range, the additive does not work as intended.

In step (2), the crystallization is carried out preferably by refrigerative cooling or evaporative cooling, more preferably by the evaporative cooling. Besides, when the crystallization is carried out by the evaporative cooling, vapor generated by evaporation may be used in the heating and dissolving process of the methionine suspension, after being pressurized by a vapor compressor to raise temperature, so as to achieve the effect of energy reuse.

The crystallizer used in step (2) may be of various forms suitable for continuous crystallization, and it is not particularly limited. For example, the crystallizer may be a stirring crystallization kettle, e.g., a stirring crystallization kettle with external circulation and a horizontal stirring crystallizer, a forced-circulating crystallizer (FC crystallizer), an OSLO crystallizer (OSLO crystallizer), and a draft-tube-baffled crystallizer (DTB crystallizer); and preferably, the continuous crystallization is carried out in an FC crystallizer, an OSLO crystallizer, and DTB crystallizer.

The present disclosure will be further illustrated with reference to the examples, but the examples described below are not intended to limit the scope of protection for the present disclosure.

Example 1

The additive used in this example was an aqueous mixture of 6 wt % of sodium methyl stearoyl taurate, 6 wt % of polyoxyethylene polyoxypropylene ether-grafted silicone oil having a molecular weight of 3,000 and an HLB value of 10, 3 wt % of hydroxyl silicone oil having a dynamic viscosity at 25° C. of 90 mm$^2$/s, and the remaining being water.

(1) To the aqueous methionate solution obtained from hydrolysis of 5-(2-methylthioethyl)-hydantoin, 300 ppm of an additive based on the aqueous methionate solution was added, and carbon dioxide was charged while stirring to precipitate a methionine crystal by means of reaction crystallization. The methionine crystal was filtered to obtain a crude methionine crystal product.

(2) The above crude methionine crystal product was fed into a stirring vessel, and an appropriate amount of water and/or crystallization mother liquor was added thereto to formulate a methionine suspension having a solid content of 11 wt %. 500 ppm of the additive based on the methionine suspension was added to the vessel, stirred and heated till the temperature in the vessel reached 100° C. and held for a period of time until the crude methionine crystal product was completely dissolved, to produce an additive-containing methionine solution with a concentration of 10 wt %. The above additive-containing methionine solution was continuously fed at 500 L/h into a 1000-L DTB crystallizer. By evaporating water under reduced pressure (vacuum degree: −0.092 MPa), the temperature in the crystallizer was maintained at 25° C. for continuous crystallization, and at the same time, the crystallization slurry was continuously discharged while controlling the liquid level constant. The crystallization slurry was filtered, washed and dried to give, at 3.6 Kg/h, a methionine crystal product (FIG. 1 shows a microscope photograph of its crystal) with a bulk density of 786 g/L.

After compressed by a vapor compressor to an absolute pressure of 0.09 MPa, the water vapor evaporated during crystallization in step (2) could be used as a heating medium for warming up when dissolving the crude methionine crystal product. Furthermore, the crystallization mother liquor obtained from the filtration of methionine crystals in the step (2) and in step (1) was used to formulate a solution of crude methionine crystal product.

The crystallization system operated continuously for 15 days without observing obvious foaming, and the crystallization process was smooth and steady.

Example 2

The additive used in this example was an aqueous mixture of 2 wt % of sodium methyl cocoyl taurate, 2 wt % of polyoxyethylene polyoxypropylene ether-grafted silicone oil having a molecular weight of 6,000 and an HLB value of 12, 1 wt % of dimethyl silicone oil having a dynamic viscosity at 25° C. of 1,500 mm$^2$/s, and the remaining being water.

(1) To the aqueous methionate solution obtained from hydrolysis of 5-(2-methylthioethyl)-hydantoin, 150 ppm of an additive based on the aqueous methionate solution was added, and carbon dioxide was charged while stirring to precipitate a methionine crystal by means of reaction crystallization. The methionine crystal was filtered to obtain a crude methionine crystal product.

Figure 2:
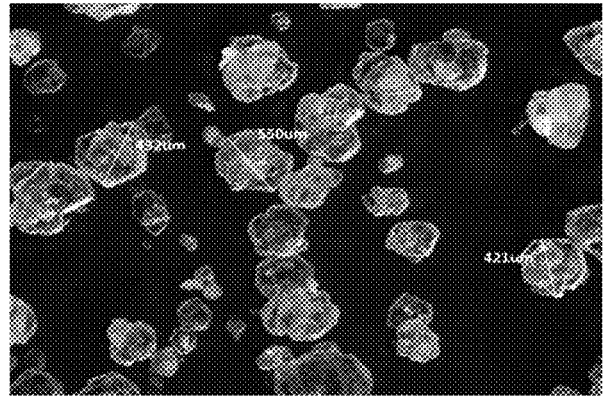

(2) The above crude methionine product was fed into a stirring vessel, and an appropriate amount of water and/or crystallization mother liquor was added thereto to formulate a methionine suspension having a solid content of 8 wt %. 200 ppm of the additive based on the methionine suspension was added to the vessel, stirred and heated till the temperature in the vessel reached 90° C. and held for a period of time until the crude methionine crystal product was completely dissolved, to produce an additive-containing methionine solution with a concentration of 11 wt %. The above additive-containing methionine solution was continuously fed at 500 L/h into a 1000-L OSLO crystallizer. By evaporating water under reduced pressure (vacuum degree: −0.088 MPa), the temperature in the crystallizer was maintained at 40° C. for continuous crystallization, and at the same time, the crystallization slurry was continuously discharged while controlling the liquid level constant. The crystallization slurry was filtered, washed and dried to give, at 1.9 Kg/h, a methionine crystal product (FIG. 2 shows a microscope photograph of its crystal) with a bulk density of 802 g/L.

After compressed by a vapor compressor to an absolute pressure of 0.1 MPa, the water vapor evaporated during crystallization in step (2) could be used as a heating medium for warming up when dissolving the crude methionine product. Furthermore, the crystallization mother liquor obtained from the filtration of methionine crystals in the step (2) and in step (1) was used to formulate a solution of crude methionine crystal product.

The crystallization system operated continuously for 15 days without observing obvious foaming, and the crystallization process was smooth and steady.

Example 3

The additive used in this example was an aqueous mixture of 3 wt % of sodium methyl lauroyl taurate, 4 wt % of polyoxyethylene polyoxypropylene ether-grafted silicone oil having a molecular weight of 5,300 and an HLB value of 11, 3 wt % of dimethyl silicone oil having a dynamic viscosity at 25° C. of 1,100 mm$^2$/s, and the remaining being water.

(1) To the aqueous methionate solution obtained from hydrolysis of 5-(2-methylthioethyl)-hydantoin, 70 ppm of an additive based on the aqueous methionate solution was added, and carbon dioxide was charged while stirring to precipitate a methionine crystal by means of reaction crystallization. The methionine crystal was filtered to obtain a crude methionine crystal product.

Figure 3:
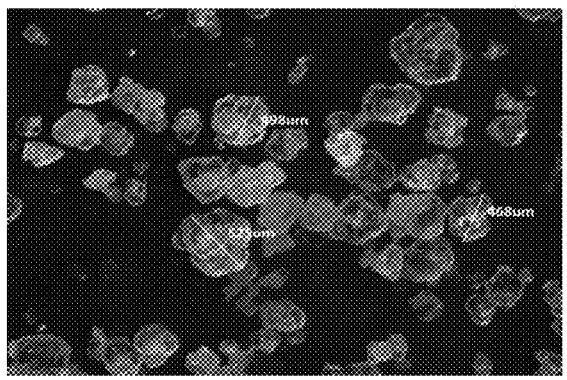

(2) The above crude methionine product was fed into a stirring vessel, and an appropriate amount of water and/or crystallization mother liquor was added thereto to formulate a methionine suspension having a solid content of 13 wt %. 400 ppm of the additive (3 wt % of sodium methyl lauroyl taurate, 4 wt % of polyoxyethylene polyoxypropylene ether-grafted silicone oil having a molecular weight of 5,300 and an HLB value of 11, 3 wt % of dimethyl silicone oil having a dynamic viscosity at 25° C. of 1,100 mm$^2$/s, and the remaining being water) based on the methionine suspension was added to the vessel, stirred and heated till the temperature in the vessel reached 110° C. and held for a period of time until the crude methionine crystal product was completely dissolved, to produce an additive-containing methionine solution with a concentration of 12 wt %. The above additive-containing methionine solution was continuously fed at 500 L/h into a 1000-L FC crystallizer. By evaporating water under reduced pressure (vacuum degree: −0.07 MPa), the temperature in the crystallizer was maintained at 65° C. for continuous crystallization, and at the same time, the crystallization slurry was continuously discharged while controlling the liquid level constant. The crystallization slurry was filtered, washed and dried to give, at 2.5 Kg/h, a methionine crystal product (FIG. 3 shows a microscope photograph of its crystal) with a bulk density of 798 g/L.

After compressed by a vapor compressor to an absolute pressure of 0.15 MPa, the water vapor evaporated during crystallization in step (2) could be used as a heating medium for warming up when dissolving the crude methionine product. Furthermore, the crystallization mother liquor obtained from the filtration of methionine crystals in the step (2) and in step (1) was used to formulate a solution of crude methionine crystal product.

The crystallization system operated continuously for 15 days without observing obvious foaming, and the crystallization process was smooth and steady.

Example 4

The additive used in this example was an aqueous mixture of 3 wt % of sodium methyl palmitoyl taurate, 3 wt % of polyoxyethylene polyoxypropylene ether-grafted silicone oil having a molecular weight of 4,200 and an HLB value of 9, 2 wt % of dimethyl silicone oil having a dynamic viscosity at 25° C. of 510 mm$^2$/s, and the remaining being water.

(1) To the aqueous methionate solution obtained from hydrolysis of 5-(2-methylthioethyl)-hydantoin, 100 ppm of an additive based on the aqueous methionate solution was added, and carbon dioxide was charged while stirring to precipitate a methionine crystal by means of reaction crystallization. The methionine crystal was filtered to obtain a crude methionine crystal product.

Figure 4:
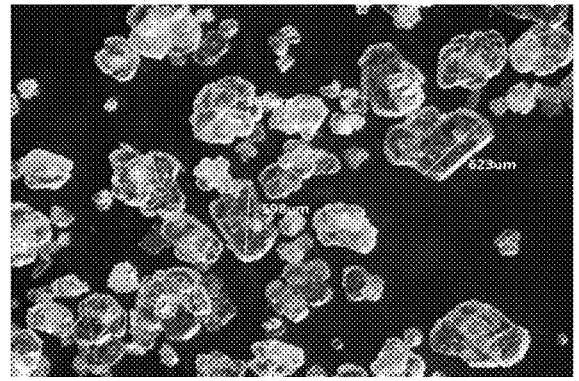

(2) The above crude methionine product was fed into a stirring vessel, and an appropriate amount of water and/or crystallization mother liquor was added thereto to formulate a methionine suspension having a solid content of 10 wt %. 250 ppm of the additive based on the methionine suspension was added to the vessel, stirred and heated till the temperature in the vessel reached 105° C. and held for a period of time until the crude methionine crystal product was completely dissolved, to produce an additive-containing methionine solution with a concentration of 13 wt %. The above additive-containing methionine solution was continuously fed at 500 L/h into a 1000-L DTB crystallizer. By evaporating water under reduced pressure (vacuum degree: −0.082 MPa), the temperature in the crystallizer was maintained at 50° C. for continuous crystallization, and at the same time, the crystallization slurry was continuously discharged while controlling the liquid level constant. The crystallization slurry was filtered, washed and dried to give, at 2.0 Kg/h, a methionine crystal product (FIG. 4 shows a microscope photograph of its crystal) with a bulk density of 791 g/L.

After compressed by a vapor compressor to an absolute pressure of 0.13 MPa, the water vapor evaporated during crystallization in step (2) could be used as a heating medium for warming up when dissolving the crude methionine product. Furthermore, the crystallization mother liquor obtained from the filtration of methionine crystals in the step (2) and in step (1) was used to formulate a solution of crude methionine crystal product.

The crystallization system operated continuously for 15 days without observing obvious foaming, and the crystallization process was smooth and steady.

Example 5

The additive used in this example was an aqueous mixture of 5 wt % of sodium methyl myristoyl taurate, 5 wt % of polyoxyethylene polyoxypropylene ether-grafted silicone oil having a molecular weight of 3,600 and an HLB value of 10.5, 2 wt % of dimethyl silicone oil having a dynamic viscosity at 25° C. of 270 mm²/s, and the remaining being water.

(1) To the aqueous methionate solution obtained from hydrolysis of 5-(2-methylthioethyl)-hydantoin, 200 ppm of an additive based on the aqueous methionate solution was added, and carbon dioxide was charged while stirring to precipitate a methionine crystal by means of reaction crystallization. The methionine crystal was filtered to obtain a crude methionine crystal product.

Figure 5:
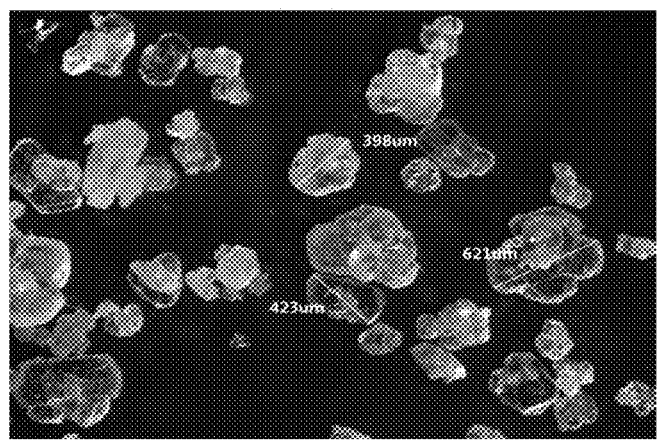

(2) The above crude methionine product was fed into a stirring vessel, and an appropriate amount of water and/or crystallization mother liquor was added thereto to formulate a methionine suspension having a solid content of 9 wt %. 400 ppm of the additive based on the methionine suspension was added to the vessel, stirred and heated till the temperature in the vessel reached 95° C. and held for a period of time until the crude methionine crystal product was completely dissolved, to produce an additive-containing methionine solution with a concentration of 14 wt %. The above additive-containing methionine solution was continuously fed at 500 L/h into a 1000-L DTB crystallizer. By evaporating water under reduced pressure (vacuum degree: −0.09 MPa), the temperature in the crystallizer was maintained at 30° C. for continuous crystallization, and at the same time, the crystallization slurry was continuously discharged while controlling the liquid level constant. The crystallization slurry was filtered, washed and dried to give, at 2.4 Kg/h, a methionine crystal product (FIG. 5 shows a microscope photograph of its crystal) with a bulk density of 795 g/L.

After compressed by a vapor compressor to an absolute pressure of 0.095 MPa, the water vapor evaporated during crystallization in step (2) could be used as a heating medium for warming up when dissolving the crude methionine product. Furthermore, the crystallization mother liquor obtained from the filtration of methionine crystals in the step (2) and in step (1) was used to formulate a solution of crude methionine crystal product.

The crystallization system operated continuously for 15 days without observing obvious foaming, and the crystallization process was smooth and steady.

What is claimed is:

1. An additive for use in a methionine preparation process, wherein the additive is a mixture comprising components A, B and C, the component A has a structure represented by the following general formula (1):

$$RCON(CH_3)CH_2CH_2SO_3Na \quad (1)$$

in formula (1), R is a saturated or unsaturated $C_7$-$C_{36}$ hydrocarbyl group;

the component B has a structure represented by the following general formula (2):

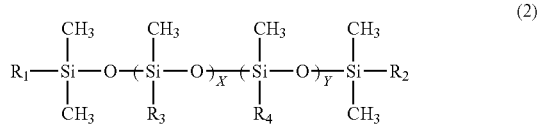

(2)

in formula (2), X and Y are each an integer of 1 to 30, $R_1$ to $R_4$ are the same as or different from one another, and each independently represent H, an $C_1$-$C_3$ alkyl group, a saturated or unsaturated aliphatic hydroxyl group, or a saturated or unsaturated polyether group, provided that at least one of $R_1$ to $R_4$ represents the saturated or unsaturated polyether group;

and the component C is silicone oil.

2. The additive for use in a methionine preparation process according to claim 1, wherein the component A is one or more of sodium methyl octanoyl taurate, sodium methyl decanoyl taurate, sodium methyl lauroyl taurate, sodium methyl myristoyl taurate, sodium methyl palmitoyl taurate, sodium methyl stearoyl taurate, sodium methyl oleyl taurate, sodium methyl linoleoyl taurate, sodium methyl linolenoyl taurate, sodium methyl erucoyl taurate, sodium methyl cocoyl taurate, sodium methyl palmitoyl taurate, sodium methyl soybean oil fatty acyl taurate, sodium methyl peanut oil fatty acyl taurate, sodium methyl sesame oil fatty acyl taurate, sodium methyl mustard oil fatty acyl taurate, sodium methyl hardened tallow fatty acyl taurate, and sodium methyl hardened vegetable oil fatty acyl taurate.

3. The additive for use in a methionine preparation process according to claim 1, wherein the component B has a molecular weight of from 1,000 to 10,000.

4. The additive for use in a methionine preparation process according to claim 1, wherein the component B has an HLB value of from 7 to 15.

5. The additive for use in a methionine preparation process according to claim 1, wherein the component B is polyether-grafted silicone oil.

6. The additive for use in a methionine preparation process according to claim 1, wherein the component C comprises one or more of dimethyl silicone oil, hydroxyl silicone oil, and hydrogen-containing silicone oil.

7. The additive for use in a methionine preparation process according to claim 1, wherein the additive is an aqueous mixture comprising the components A, B and C, and based on a total mass of the additive, the content of the component A is from 1 to 8 wt %, and the content of the component B is from 0.5 to 8 wt %, and the content of the component C is from 0.5 to 4 wt %.

8. A method for preparing methionine, comprising:
subjecting methionine to crystallization and/or recrystallization in the presence of the additive according to claim 1.

9. The preparation method for methionine according to claim 8, comprising the steps of:

(1) subjecting an aqueous methionate solution obtained from hydrolysis of 5-(2-methylthioethyl)-hydantoin to reaction crystallization in the presence of an additive and carbon dioxide, to obtain a crude methionine crystal product; and (2) forming a methionine suspension from the crude methionine crystal product, water and/or crystallization mother liquor, adding an additive, and recrystallizing an additive-containing methionine solution, to obtain a methionine crystal product.

10. The preparation method for methionine according to claim 9, wherein an amount of the additive in the step (1) is from 50 ppm to 500 ppm based on a total mass of the aqueous methionate solution.

11. The preparation method for methionine according to claim 9, wherein the methionine suspension in the step (2) has a concentration of from 8 to 15 wt %.

12. The preparation method for methionine according to claim 9, wherein an amount of the additive in the step (2) is from 100 ppm to 1,000 ppm based on a total mass of the methionine suspension.

13. The preparation method for methionine according to claim 9, wherein in the step (2), the crystallization is carried out by means of refrigerative cooling or evaporative cooling; and when the crystallization is carried out by the evaporative cooling, vapor generated by evaporation is pressurized by a vapor compressor to raise temperature, and is then used in a heating and dissolving process of the methionine suspension.

14. The preparation method for methionine according to claim 9, wherein a crystallizer used in the step (2) includes a stirring crystallization kettle, a forced-circulating crystallizer, an OSLO crystallizer, and a draft-tube-baffled crystallizer.

15. The additive for use in a methionine preparation process according to claim 1, wherein the component B has a molecular weight of from 3,000 to 6,000.

16. The additive for use in a methionine preparation process according to claim 1, wherein the component B has an HLB value of from 9 to 12.

17. The additive for use in a methionine preparation process according to claim 1, wherein the component C has a dynamic viscosity at 25° C. of 90 mm$^2$/s to 1,500 mm$^2$/s.

18. The additive for use in a methionine preparation process according to claim 1, wherein the polyether group is a group represented by the following general formula (3):

$$—C_3H_6O(C_2H_4O)_a(C_3H_6O)_bR_0 \qquad (3)$$

in formula (3), a represents an integer of 0 to 50, b represents an integer of 0 to 50, and $R_0$ represents H, an alkyl group, an acyloxyl group, or an alkoxyl group.

19. The additive for use in a methionine preparation process according to claim 1, wherein the content of the component A is from 2 to 6 wt %, the content of the component B is from 2 to 6 wt %, and the content of the component C is from 1 to 3 wt %.

20. The preparation method for methionine according to claim 9, wherein an amount of the additive in the step (1) is from 70 ppm to 300 ppm based on a total mass of the aqueous methionate solution.

* * * * *